United States Patent [19]

Jones

[11] 4,243,025

[45] Jan. 6, 1981

[54] CERVICAL ADJUSTING UNIT

[75] Inventor: Donald E. Jones, Mullins, S.C.

[73] Assignee: Life Chiropractic College, Inc., Marietta, Ga.

[21] Appl. No.: 900,195

[22] Filed: Apr. 26, 1978

[51] Int. Cl.[3] .................................................. A61F 5/00

[52] U.S. Cl. ........................................ 128/70; 269/325; 269/328; 297/409; 248/123.1

[58] Field of Search ........................ 128/70, 71, 72, 73, 128/74, 75, 78, 69; 269/223, 324, 326, 327, 325, 328; 297/407, 408, 409, 410; 248/648, 657, 651, 646, 325, 123.1, 280.1

[56] References Cited

U.S. PATENT DOCUMENTS

| | | | |
|---|---|---|---|
| 69,135 | 9/1867 | Snowden | 297/409 |
| 132,255 | 10/1872 | Coates | 297/409 |
| D. 223,419 | 4/1972 | Pettibon | D24/3 |
| 602,571 | 4/1898 | Bowers | 269/324 |
| 978,760 | 12/1910 | Langworthy | 128/71 |
| 2,048,220 | 7/1936 | Redding | 128/69 |
| 2,051,508 | 8/1936 | Wildeboer | 248/123.1 |
| 2,456,277 | 12/1948 | Heitz-Boyer | 269/323 |
| 2,753,233 | 7/1956 | Rock | 269/328 |
| 3,188,079 | 6/1965 | Boetcker et al. | 269/328 |
| 3,226,106 | 12/1965 | Johnson et al. | 269/325 |
| 3,329,423 | 7/1967 | Kleinman | 269/324 |
| 3,771,518 | 11/1973 | Greissing | 128/71 |
| 4,033,339 | 7/1977 | Roberts et al. | 128/73 |

FOREIGN PATENT DOCUMENTS

| | | | |
|---|---|---|---|
| 562676 | 12/1957 | Belgium | 248/123.1 |
| 615384 | 1/1949 | United Kingdom | 248/123.1 |

*Primary Examiner*—Robert W. Michell
*Assistant Examiner*—Arthur S. Rose
*Attorney, Agent, or Firm*—Jones, Thomas & Askew

[57] ABSTRACT

An improved cervical adjusting unit for applying a specifically directed force to the cervical spine of a patient to correct subluxations of the cervical spine, comprising an adjustable table for supportably positioning a patient in side posture thereon with the cervical spine in a preselected and prestressed configuration, the table including a first horizontal support surface for the pelvis and legs of the patient, a second adjustable support surface for supporting and positioning the thoracic and shoulder portions of the patient, and a headpiece which is adjustable in multiple directions to position the head of the patient; and a force applicator unit adjacent the headpiece of the table for directing a predetermined force against the cervical spine of the patient by means of a force-imparting stylus, the stylus being supported for universal adjustment with respect to the patient in a positionally adjustable force applicator head mounted on the outer end of an adjustable parallelogram section which is attached for rotation to a support column of the unit.

7 Claims, 7 Drawing Figures

CERVICAL ADJUSTING UNIT

This invention relates to an improved apparatus for use in the field of chiropractic, and, more particularly, to an improved apparatus for more accurately correcting subluxations of the cervical spine.

BACKGROUND OF THE INVENTION

The art and science of chiropractic is directed to a system or practice of adjusting the joints, especially of the spine, for the curing of disease. Subluxations, or misalignments, of the vertebrae of the spine create abnormal conditions which reduce the capability of the body to function in proper manner. Subluxations occlude neural spaces of the spine and possess the capability of causing nerve interference. Subluxation is the condition of a vertebrae that has lost its proper juxtaposition with the one above or the one below it, or both, which impinges nerves and interferes with the transmission of mental impulses. Therefore, it is an object of chiropractic to correct subluxations, or misalignments, of the spine by the application of force to realign the vertebrae.

There are four functioning units of the spine, the cervical, thoracic, lumbar, and sacro-coccygeal sections, which interact with one another in normal functioning. The cervical spine as a functioning unit includes the occiput, the seven cervical vertebrae, and the first two dorsal vertebrae, commonly known as the normal cervical lordosis. In correcting subluxations of the cervical spine, it is a known practice in chiropractic to apply an external, specifically directed force to the transverse process of the atlas, or top vertebra, of the cervical spine which is transmitted through all of the vertebra of the functional cervical spine to produce realignment. One prior known method of application of such force has been accomplished by the use of a cervical adjusting unit comprising a patient support table having an adjustable headpiece on which a patient is placed in a desired position for introduction of the force. Such a device is understood to be exemplified by Pettibon U.S. Pat. No. Des. 223,419. The force is applied to the desired vertebra by means of a mechanical apparatus having a metal rod, or stylus, the point of which is positioned in a precise location against the desired vertebra of the patient's cervical spine and caused to move through a precise distance in a specific direction, thus transmitting the point force into the cervical spine for correction of subluxations which may be present at a given location in the functional cervical spine.

OBJECTS OF THE INVENTION

It is an object of the present invention to provide an improved cervical adjusting unit, or machine, for more accurately positioning the patient and applying the force to correct subluxations of the cervical spine.

It is another object of the present invention to provide an improved patient support table comprising adjustable patient-supporting sections for more precisely orienting the patient for the introduction of a corrective force into the cervical spine of the patient.

It is further object of the invention to provide improved cervical adjusting apparatus including patient support table, in combination with a force applicator device wherein the force applicator head of the device may be more easily adjusted and precisely positioned by the chiropractor during treatment to direct the predetermined force vector in any predetermined direction relative to the preselected position of the spine of the patient.

BRIEF DESCRIPTION OF THE INVENTION

The cervical adjusting unit of the present invention comprises, in its broad aspects, a table for supporting a patient in side posture including a fixed pelvic support section, an adjustable shoulder support section, and an adjustable headpiece wherein, by adjustment of the table, the patient may be accurately positioned with the cervical spine in a predetermined stressed condition to facilitate correction of the total cervical subluxation upon application of an external force. The cervical adjusting unit includes a force-applying section containing a stylus which may be easily and accurately positioned relative to the patient's body to direct the corrective force in any desired direction and at a preselected point on the cervical spine.

BRIEF DESCRIPTION OF THE DRAWINGS

The invention will be better understood and the above as well as other objects of the invention will become more apparent from the following detailed description of a preferred embodiment of the invention, when taken with the accompanying drawings, in which.

DETAILED DESCRIPTION OF PREFERRED EMBODIMENT

Figure 1:
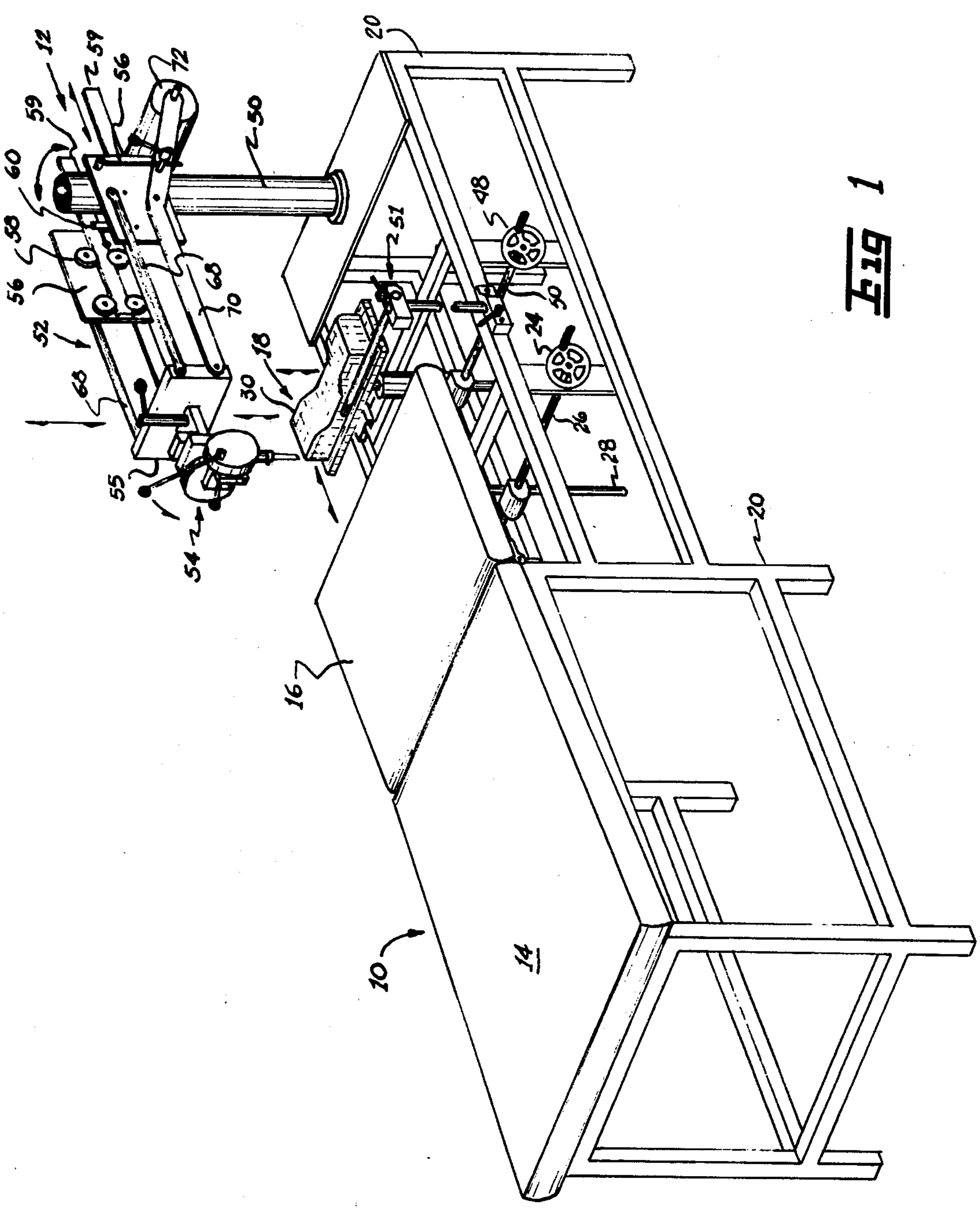
FIG. 1 is a perspective view of the cervical adjusting unit of the present invention.

As best seen in FIG. 1, the cervical adjusting unit of the invention comprises a body support table 10 and a force-applicator section, or unit, 12. Table 10 comprises a fixed horizontal, section 14 for supporting the pelvic portion and legs of a patient, a second, adjustable section 16 for supporting and adjustably positioning the thoracic and shoulder portion of the patient, and headpiece 18 for supporting and adjustably positioning the head of the patient prior to application of a corrective force from the applicator unit 12. Patient supporting surfaces of sections 14, 16, and 18 are suitably cushioned, as with a covered rubber or plastic foam pad, and the sections are suitably mounted on a frame 20.

Figure 2:
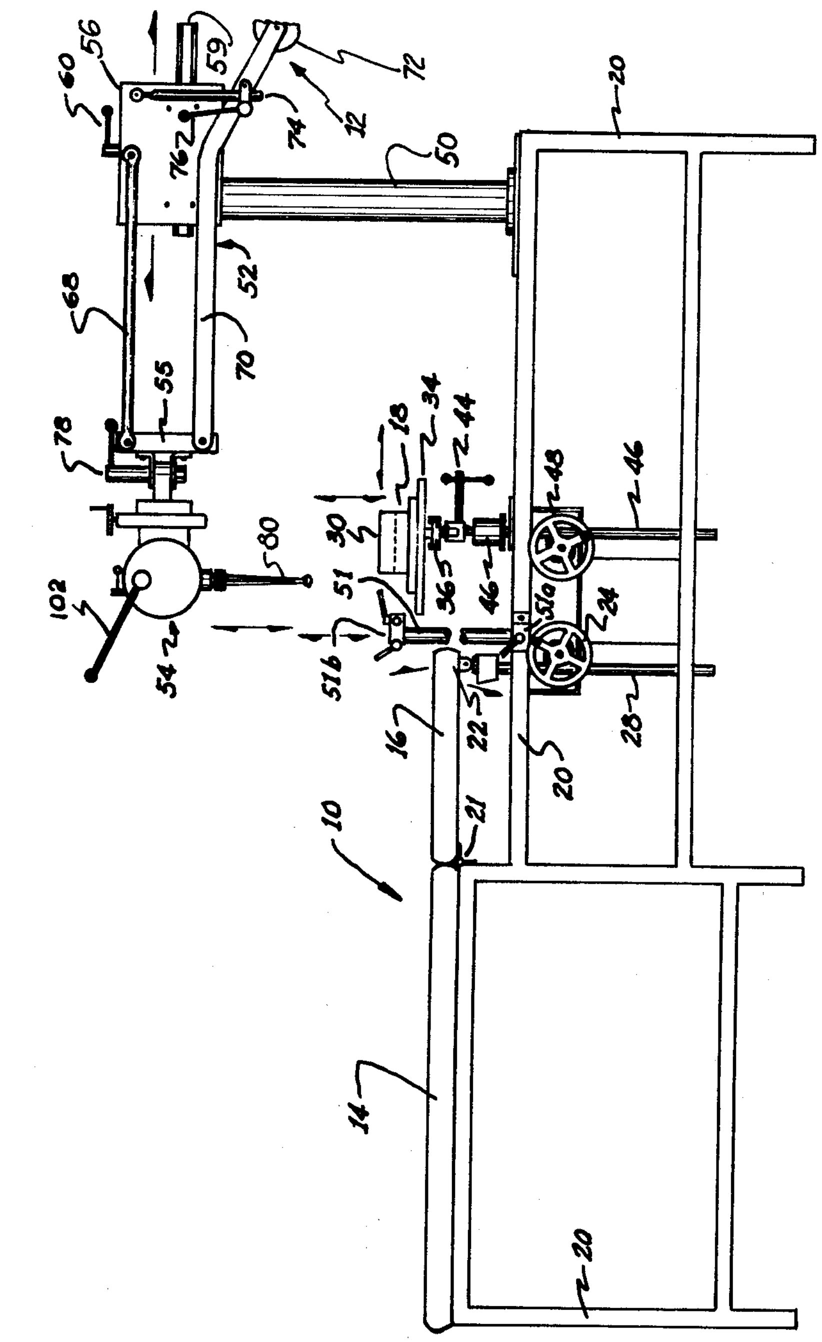
FIG. 2 is a schematic side elevation view of the unit shown in FIG. 1.

As seen in FIG. 2, horizontal pelvic support section 14 is attached in fixed position to the frame, and one end of shoulder support section 16 is pivotally hinged by one or more hinge members 21 to the adjacent end of pelvic support section 14 to permit pivotal movement of section 16 about a horizontal axis extending transverse to the longitudinal axis of table 10. For adjustment of the shoulder section, the free end 22 of the shoulder section 16 may be vertically raised and lowered by means of crank wheels on each side of table 10, one of which 24 is shown, attached by a connecting rod 26 (FIG. 1) and gear train to a conventional jack mechanism 28 which is suitably supported on the frame 20 and is pivotally connected to the undersurface of shoulder section 16 to raise or lower end 22 of section 16 through a vertical distance of approximately 6 inches.

Figure 4:
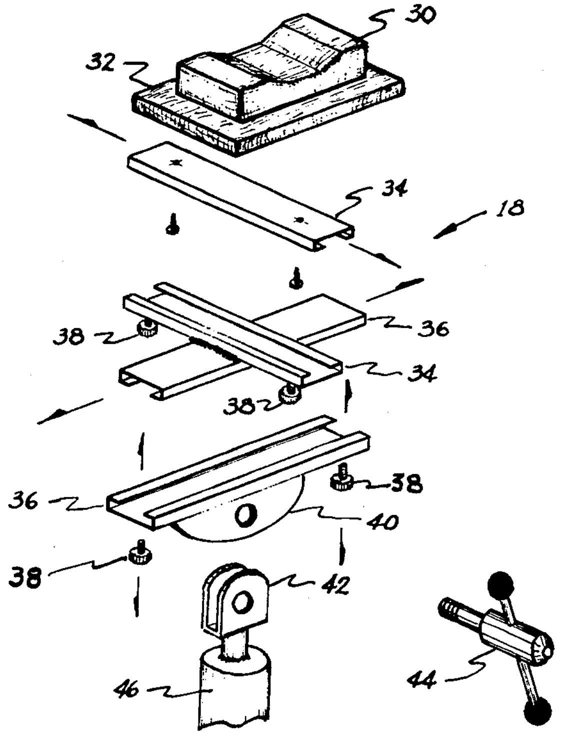
FIG. 4 is an enlarged perspective, exploded view of the headpiece of the patient support table of the cervical adjusting unit, showing in more detail the means for adjusting the position of the headpiece.

As best seen in FIGS. 1, 2, and 4, headpiece 18 of table 10 comprises a cushioned head-supporting surface 30 having a recessed mid-portion to comfortably accommodate the head of the patient when lying in a side posture on table 10. Cushioned member 30 has a base plate 32 supportably attached to first and second pairs of cooperating channel slide elements 34, 36 extending, respectively, in parallel and transverse directions to the longitudinal axis of the table. Lock knobs 38 are provided for maintaining the position of the slide elements after adjustment. The lower slide element of pair 36 is pivotally attached by cooperating elements 40, 42 (FIG. 4) and a locking handle 44 to the upper end of a jack mechanism 46 mounted on frame 20, and the jack is operated by crank wheels on each side of the table, one of which 48 is shown, through a connecting rod 50 to adjustably raise and lower the headrest 30 approximately 6 inches. Thus, by means of slide elements 34, 36, pivot elements 40, 42 and jack mechanism 46, the headpiece of the table may be adjustably positioned in longitudinal, transverse, and vertical directions with respect to the table, as well as be pivotally adjusted from side to side about a horizontal axis parallel to the longitudinal axis of the table to locate the head of the patient in a desired position for the delivery of an adjustic thrust, or corrective application of force into the cervical spine.

To further assist in precisely positioning the cervical spine in a selected prestressed condition for reception of a corrective force from the force applicator unit 12, table 10 of the cervical adjusting unit is provided with an auxilliary stress vertebra support member 51 (FIG. 1) comprised of two rigid rods disposed at right angles to form an L-shaped bracket which may be supportably attached to and removed from the frame 20 of the table by a clamp 51*a*. As seen in FIG. 1, support member 51 may be positioned on frame 20 on either side of the table between the adjustable shoulder support section 16 and headpiece 18 for stressing the cervical spine and aiding in prestressing same so that the applied force will be properly dispersed along the entire length of the functional cervical spine. The height of the stress vertebra support member 51 relative to the upper surface of the table may be adjusted by clamp 51*b* and member 51 is employed to engage the cervical spine either above or below the neck of the patient to accurately position the spine in situations where upper and lower stress subluxations of the cervical spine are significantly different in magnitude and/or direction.

Figure 3:
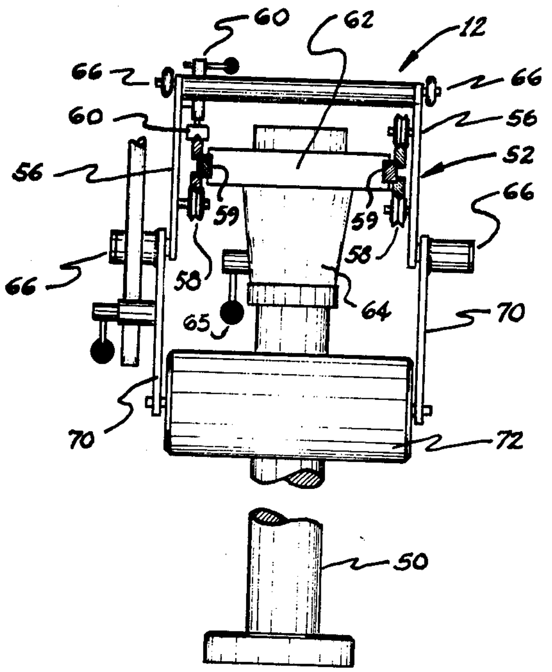
FIG. 3 is an enlarged right end elevation view of the force-applying section of the cervical adjusting unit as seen in FIG. 2.

As best seen in FIGS. 1, 2, and 3, force applicator unit 12 generally comprises a vertical support column 50 attached to frame 20, an adjustable parallelogram section 52 attached for rotational movement about the upper end of support column 50, and a force applicator head 54 supportably attached to an outer face plate 55 of the parallelogram section 52. The other end of parallelogram section 52 comprises a pair of spaced vertical plates 56 each having four guide rollers 58 which are mounted on horizontal, spaced trackways 59 to permit sliding horizontal movement of the parallelogram section relative to the support column 50 and table 10. A locking handle 60 (FIG. 4) is provided to frictionally engage one of the trackways 59 and maintain the parallelogram section 52 in a selected location along the trackways 59 after positioning. Trackways 59 are supportably attached by a horizontal plate 62 (FIG. 3) to a central collar 64 with locking handle 65 which surrounds the upper end of support column 50 to enable the parallelogram section and applicator head 54 to be rotated about the vertical axis of support column 50, as previously mentioned.

Pivotally attached by pins 66 (FIG. 3) on the outside face of each vertical side plate 56 are upper spaced, parallel rods 68 and lower parallel lever arms 70 which, as shown in FIGS. 1 and 2, extend outwardly from support column 50 toward table 10. Pivotally attached to the outer ends of the parallel rods and lever arms is face plate 55, and the lower parallel lever arms 70 have articulated portions extending rearwardly therefrom which support a counterweight 72. Thus, parallelogram section 52 may be pivoted as a unit upwardly and downwardly about pivotal connections to vertical plates 56 while at all times maintaining face plate 55 in a vertical plane. The parallelogram section 52 may be locked in a desired position of pivotal upward and downward adjustment by means of a rod 74 which is pivotally attached to the face of vertical plate 56 and is slidably received in a gripper element with locking handle 76 which frictionally engages rod 74 to fix the position of the section.

Figure 5:
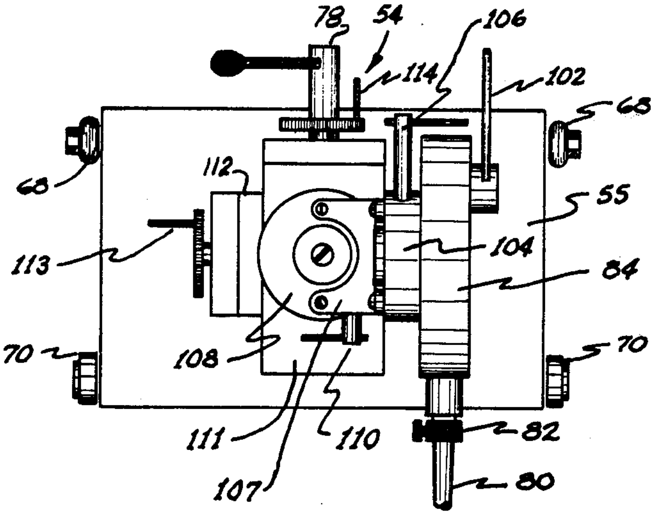
FIG. 5 is an enlarged front elevation view of the force applicator head of the unit, as seen in FIG. 1.
Figure 6:
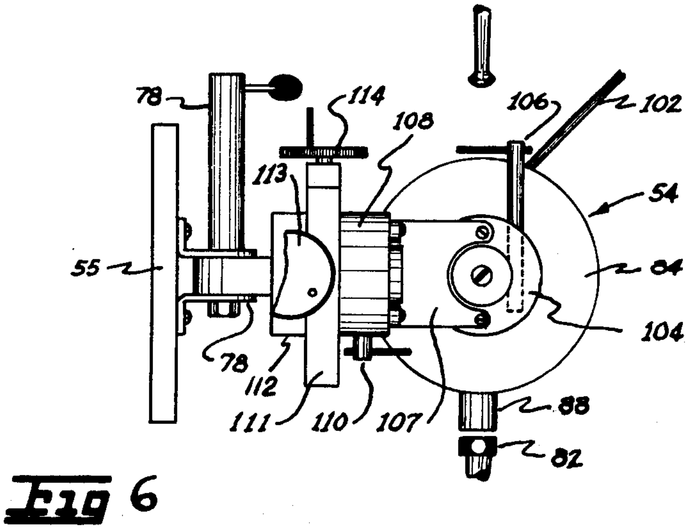
FIG. 6 is a left side elevation view of the force applicator head of FIG. 5.
Figure 7:
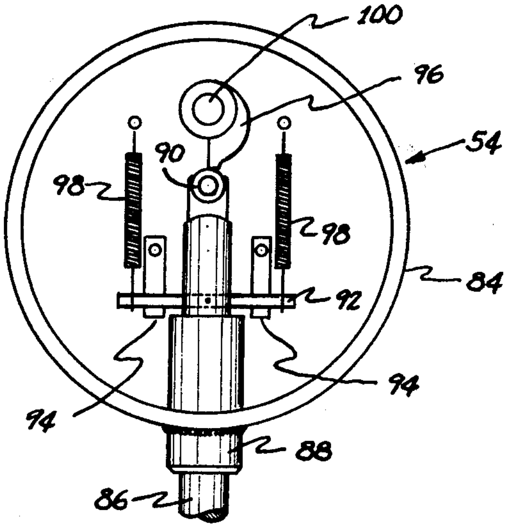
FIG. 7 is an enlarged right side, elevational view of the force applicator head of FIG. 5 with cover plate of the applicator housing removed.

As seen in FIGS. 1 and 6, force applicator head 54 of unit 12 is supportably mounted on face plate 55 for rotational adjustment about a vertical axis by means of a clevis and locking handle 78. As best seen in FIG. 5, the force application head 54 includes an elongate stylus 80 which is removably attached by a lock sleeve 82 to an actuator mechanism located in a circular housing 84. As seen in FIG. 7, the actuator mechanism comprises an actuator rod 86 slidably mounted in a sleeve bearing 88 and rod 86 has a cam follower 90 at its upper end. Rod 86 is axially reciprocated in bearing 88 and guided in its movement by means of a support bracket 92 and guide elements 94 attached to housing 84. Cam follower 90 is urged upwardly into engagement with an actuator cam 96 by spring elements 98. Cam 96 is rotatable about a central pin 100 by a manually operated handle 102. Thus movement of operating handle 102 by the chiropractor causes the end of stylus 80 to move outwardly in axial direction from housing 84 through a predetermined distance and at a velocity which is controlled by the movement of the handle 102 and the cam configuration.

As seen in FIG. 5, stylus actuator housing 84 is mounted for rotational adjustment about an axis perpendicular to the longitudinal axis of stylus 80 by means of a supporting protractor disk 104 with pivot pin and locking handle 106. Disk 104 is attached by a bracket 107 to a second protractor disk 108 with pivot pin and locking handle 110 which permits rotational adjustment of actuator housing 84 and stylus 80 about a horizontal axis perpendicular to both the longitudinal axis of the stylus and the axis of rotation of the stylus housing 84 through disk 104. Protractor disk 108 is operatively attached to the support clevis 78 through a pair of fine adjustment units 111 and 112 each of which has a rotatable hand wheel 113, 114 which is rotatable to adjust the position of the stylus housing and the stylus 80 in vertical and horizontal linear directions relative to face plate 55. Although not shown, hand wheels 113, 114 are connected to suitable gear train arrangements within units 111, 112, and such adjusting units are, for example, commercially available under the trademark "Unislide" manufactured by Velmex Inc. of New York.

From the foregoing description, it can be seen that the force applying stylus 80 of the force actuator head 54 of actuator unit 12 may be rotatably positioned relative to face plate 55 about (1) a vertical axis through clevis 78, (2) a first horizontal axis through protractor disk 108, and (3) a second axis perpendicular thereto through protractor disk 104. Stylus 80 further may be adjustably positioned in horizontal and vertical linear directions relative to face plate 55 by adjusting units 111 and 112. Thus the stylus can be universally positioned relative to the supporting face plate 55 for actuation by operating lever 102 in any direction. Likewise, the entire force actuator head 54 may be positioned relative to the body of the patient by means of parallelogram section 52 and its rotational adjustment about support column 50.

As can be seen, the various locking handles of the adjustable connections of the force applicator unit 12, as well as the hand wheels of the shoulder section 16 and headrest 18 of the table 10 are readily accessible to the chiropractor when standing beside the table to accurately and quickly position the patient on the table in proper prestressed condition, and to accurately and quickly locate the force-applying stylus of the applicator unit 12 in any desired position relative to the patient's cervical spine on table 10.

Although the invention has been described by specific reference to the embodiment shown in the drawings, it should be understood that modifications may be made therein without departing from the scope of the invention. For example, the elevating jacks for the headpiece and shoulder supporting surface of the table may be operated by electrical motors, with controls therefor conveniently located for access by the chiropractor, if desired.

That which is claimed is:

1. An improved chiropractic cervical adjusting unit for applying a specifically directed force to the cervical spin of a patient, said unit including a frame, an elongate adjustable table mounted on said frame for supportably receiving and positioning a patient in a preselected side posture orientation thereon, said table including a first horizontal support surface for receiving the pelvis and legs of the patient, a second support surface adjacent said first horizontal support surface for supportably receiving the thoracic and shoulder portions of the patient, means pivotally connecting said second support surface with respect to said first horizontal support surface for pivotal movement of said second support surface about a horizontal axis generally perpendicular to the longitudinal axis of said table, means operatively connected to said second support surface for adjustably positioning said second support surface about its pivotal connection to said first horizontal support surface upwardly and downwardly relative to the plane of said first horizontal support surface, a headpiece mounted on said frame and located adjacent said second support surface across from said first horizontal support surface for supportably receiving the head of a patient, means operatively connected to said headpiece for adjustably positioning the headpiece relative to said first and second support surfaces, rotationally about an axis parallel to the longitudinal axis of said table and linearly in directions parallel and perpendicular to said longitudinal axis of said table, and an auxiliary support member for engaging the upper or lower side portions of the neck of a patient in side posture on said table to facilitate prestressing the cervical spine of the patient, said auxiliary support member comprising an elongate generally horizontal rod, means for removably attaching said rod to said frame selectively on either side of said table to position said rod between said second support surface and said headpiece, and means for adjustably positioning the height of said rod relative to said said second support surface and said headpiece to engage the upper or lower side portion of the neck of a patient on said table to prestress said cervical spine in a desired direction.

2. Apparatus as defined in claim 1 wherein said means operatively connected to said second support surface for adjustably positioning said second support surface comprises jack means attached to said frame and said second support surface for adjustably elevating and lowering said second support surface; and said means operatively connected to said headpiece for adjustably positioning the headpiece comprising jack means mounted on said frame and connected to said headpiece for raising and lowering said headpiece in a vertical direction.

3. Apparatus as defined in claim 2 wherein each of said jack means includes manually operable hand wheels supportably attached to said frame for operation of said jack means and located on each side of said table below the body support surfaces thereof for access by an operator standing on either side of said table adjacent said second support surface.

4. An improved chiropractic cervical adjusting unit for applying a specifically directed force to the cervical spine of a patient lying in side posture on a support surface including a support surface, a positionally adjustable force applicator means located adjacent said support surface, said applicator means comprising a generally vertical support column, an adjustable parallelogram support section mounted on said column for rotational movement about a vertical axis; said parallelogram support section pivotably mounted at said support column about horizontal axes, means for moving said horizontal axes horizontally toward and away from said support column, said parallelogram support section extending outwardly from said column and including a generally vertical support plate at the outer end thereof, and said parallelogram support section including means for pivotally moving said support plate upwardly and downwardly with respect to said support column about said horizontal axes whereby said support plate is movable upwardly and downwardly about horizontal axes adjacent said support column and is movable toward and away from said support column while remaining in a substantially vertical attitude, a force applicator head mounted on said plate for pivotal movement about a vertical axis, said applicator head comprising an elongate stylus having an end surface for contacting the body of a patient to impart a particularly directed force against the cervical spine of the patient, means for directing said stylus in its axial direction through a predetermined distance with respect to said support plate to apply said force, and means for rotatably positioning said stylus about a first horizontal axis and a second axis perpendicular to said first horizontal axis and perpendicular to the longitudinal axis of said stylus, whereby said stylus may be universally adjusted to impart said force against the patient in any preselected direction, and a counterweight mounted on said parallelogram support section at a position which balances said support plate and said force applicator head about the horizontal axes of said parallelogram support section at said support column.

5. An improved chiropractic cervical adjusting unit for applying a specifically directed force to the cervical spine of a patient, said unit including an elongate adjustable table for supportably receiving and positioning a patient in a preselected side posture orientation thereon, a headpiece located adjacent an end of said table for supportably receiving the head of a patient, and means operatively connected to said headpiece for adjustably positioning the headpiece relative to said table rotationally about an axis parallel to the longitudinal axis of said table and linearly in directions parallel and perpendicular to said longitudinal axis of said table, positionally adjustable force applicator means located adjacent said headpiece for applying a specifically directed force at a particular location on the cervical spine of a patient lying on said table, said force applicator means comprising a generally vertical support column, an adjustable parallelogram support section movably mounted at one end portion thereof on said support column for rotational movement about a vertical axis, means for moving said one end portion of said parallelogram support section horizontally toward and away from said support column, said parallelogram support section extending outwardly from said column and having an outer end positionable in general proximity to said table headpiece, said parallelogram support section including a generally vertical support plate at said outer end thereof, and means for pivotally moving said support plate upwardly and downwardly with respect to said support column about a horizontal axis adjacent said support column while maintaining said support plate in a vertical attitude, a force applicator head, means mounting said force applicator head on said support plate for pivotal movement about a vertical axis, said force applicator head comprising an elongate stylus having an end surface for contacting the body of a patient on said table to impart a particularly directed force against the cervical spine of the patient on said table, means for directing said stylus in its axial direction through a predetermined distance with respect to said support plate to apply said force, and means for rotatably positioning said stylus about a first horizontal axis and about a second axis perpendicular to said horizontal axis and about an axis perpendicular to the longitudinal axis of said stylus, whereby said stylus can be adjustably located to impart said force against the patient on the table in any direction.

6. Apparatus as defined in claim 5 wherein said applicator head further includes means for adjustably positioning said stylus in vertical and horizontal linear directions relative to said vertical support plate at one end of said parallelogram support section.

7. Apparatus as defined in claim 5 wherein said parallelogram support section further includes means for adjustably positioning said vertical support plate in a horizontal retilinear direction relative to said support column.

* * * * *